United States Patent [19]

Wardlaw

[11] 4,227,528
[45] Oct. 14, 1980

[54] AUTOMATIC DISPOSABLE HYPODERMIC SYRINGE

[76] Inventor: Stephen C. Wardlaw, 128 Sunset Hill Dr., Branford, Conn. 06405

[21] Appl. No.: 972,756

[22] Filed: Dec. 26, 1978

Related U.S. Application Data

[63] Continuation-in-part of Ser. No. 955,773, Oct. 30, 1978, abandoned.

[51] Int. Cl.³ .............................................. A61M 5/00
[52] U.S. Cl. .......................... 128/218 A; 128/218 F; 128/218 D
[58] Field of Search ........... 128/218 R, 218 F, 218 D, 128/215, 213, 216, 220

[56] References Cited

U.S. PATENT DOCUMENTS 3,605,744   9/1971   Dwyer ............................. 128/218 F

FOREIGN PATENT DOCUMENTS 585862  10/1959  Canada .................................. 128/218 F
2461272  7/1976  Fed. Rep. of Germany ....... 128/218 F
282268  12/1964  Netherlands .......................... 128/218 F

*Primary Examiner*—John D. Yasko
*Attorney, Agent, or Firm*—William W. Jones

[57] ABSTRACT

A hypodermic syringe for use in situations wherein an experienced medical person may not be available to administer an injection. The device is sterile and watertight and may be carried about on one's person without special precautions being taken. Upon use, substantially instantaneous but sequentially controlled skin penetration and injection are achieved. The syringe can be used only once, and has a shelf life of more than one year with most medicaments.

4 Claims, 11 Drawing Figures

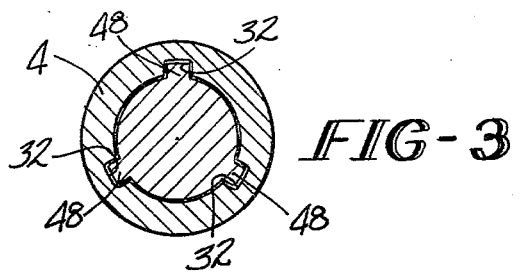
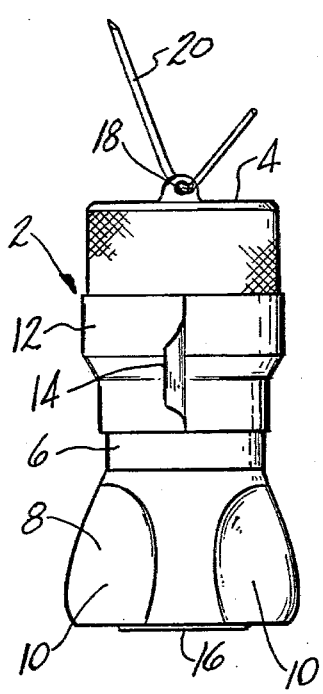
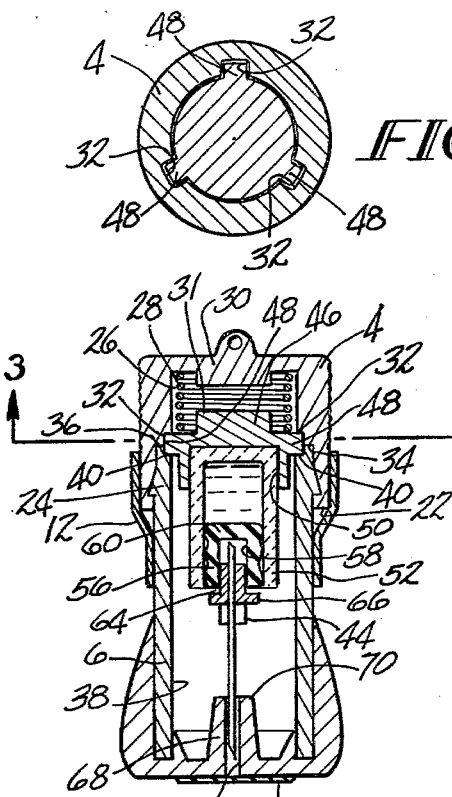
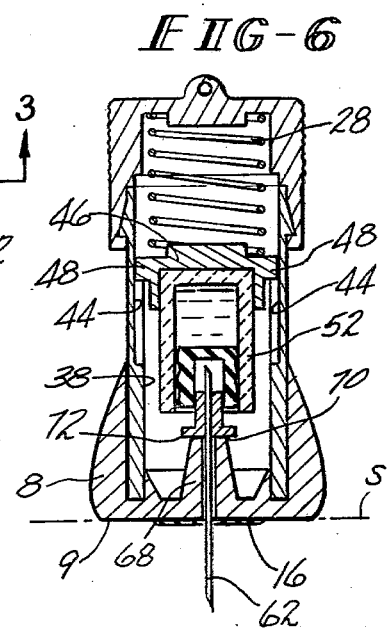
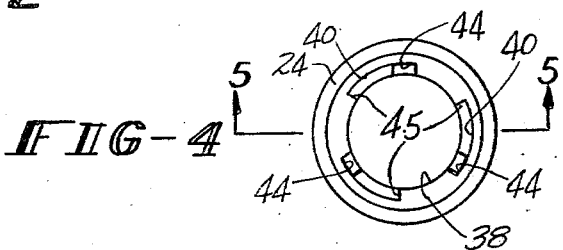
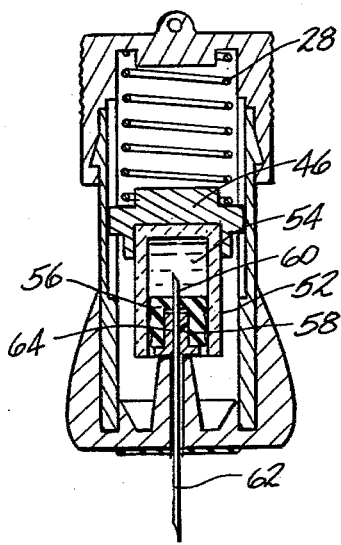
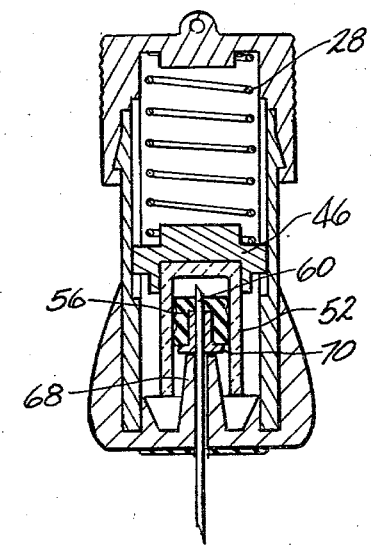
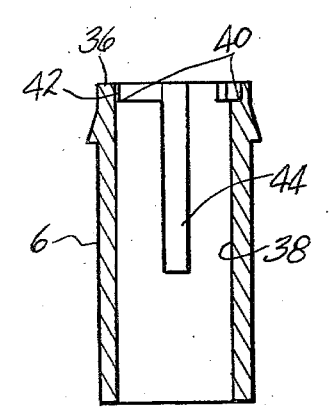

AUTOMATIC DISPOSABLE HYPODERMIC SYRINGE

This application is a continuation-in-part of U.S. patent application Ser. No. 955,773, filed Oct. 30, 1978 now abandoned.

This invention relates to an automatic, disposable hypodermic syringe which is specifically adapted for use by a layman who has had no specific training or experience in administering an injection. More particularly, the invention relates to a syringe which can be used only once.

There are a number of uses to which such a syringe can be usefully put. For example, such a syringe can be carried about and used in emergency situations by persons who are highly allergic to venomous insect stings, or who suffer from other miscellaneous allergies which result in life threatening angioedema unless proper medication is promptly administered sub-cutaneously. Another use for such a syringe is to inject a medicating dose of atropine to counter-act the effects of nerve gas in the military. Other uses are also apparent, for example: for self-injecting unit doses of insulin by diabetics; injection of pain-killing medications for cancer patients; injection of anti-emetics to control nausea and vomiting in chemotherapy patients; and for administering numerous other injections requiring standard doses of medication.

The prior art is replete with mechanisms which are designed to automatically administer an injection without the need of consciously inserting the needle into one's flesh prior to administering the injection. These automatic syringes share one common feature, e.g., all of them utilize a retracted needle which is released and driven into the user's flesh by means of a spring, a compressed gas charge, or the like. At the same time, the prior art automatic syringes possess many drawbacks, for example: complexity of design; unsuitability for storing a medicament for an extended period of time prior to use; inability to retain sterility over an extended period of time; capability of being reused for non-intended purposes, e.g., by drug addicts. Other compact, throw-away syringes have been disclosed in the prior art for use in emergency situations as described first above; however, these syringes are, for the most part, not automatic, and require the user to push the needle into his flesh when used. One additional drawback which is found in most of the prior art automatic or compact syringes is that the injection sequence is uncertain and can vary from one use to the next.

In order to provide an automatic, disposable hypodermic syringe which can be used only once to administer an injection, several parameters must be concurrently met. Firstly, the number of parts must be minimized and for the most part readily manufactured by such means as injection molding of plastic, or the like. Secondly, the device should be capable of being assembled primarily by means of automated procedures to lower costs because the device is disposable after a single use. Thirdly, the ampuole and the internal components of the device must be separably sterilizable because procedures which are necessary to sterilize the medication and ampuole are generally destructive of the resinous material from which the majority of the remainder of the device is made. Once assembled, the device, both the ampuole and the housing-operating mechanism must retain their sterility and be both air-tight and water-proof. Since the device must possess a shelf life in the order of about one year to be useful for emergency situations over a reasonable period of time, the medication must be maintained completely separate and sealed from all of the other components of the device and must only contact the ampuole and its closure prior to administering the actual injection. This integrity of the medication is necessary because the medication can itself support the growth of organisms, and would thus itself become a source of disease. Furthermore, the medication must be kept out of contact with such materials such as the metal needle prior to injection, since long periods of exposure to such materials can cause the medication to lose its effectiveness. The device must also provide protection for the needle and medication ampoule so that the delicate needle and ampoule will not be harmed by rough handling, or by accidental occurrences, such as, for example, if the device were to be dropped. Finally, since the device of this invention is contemplated for use in emergency situations, it must operate each time in a predetermined dependable manner, which minimizes the chance of malfunction.

I have devised a novel contamination-resistant hypodermic syringe which can be carried about safely by a potential user. The syringe of this invention can be made small enough to be worn inobtrusively on a chain or the like draped around the user's neck. The syringe is maintained in a sterile condition without requiring any special packaging, is also maintained in a water-tight condition, so that it can even be worn while swimming or bathing, if desired. A syringe made in accordance with this invention can be operated quickly and effectively by merely pressing one end thereof against the skin and manually manipulating the device to inject the medication.

The hypodermic needle is recessed in the syringe and the surface which is pressed against the skin is preferably flat with no uncomfortable sharp protruding parts. The needle is spring-loaded and can be manually released so as to quickly pierce the flat surface of the syringe and the skin, and inject the medication into the flesh of the user. The entire injection is accomplished in less than one second. Release of the needle is preferably accomplished by a natural and quickly executed motion, such as by twisting the syringe, or the like.

Since the dependable storage life of an effective dose of adrenalin is approximately one year, it is contemplated that one or more of the syringes of this invention will be retained by a potential user for such period and, if the same is not used, it will be discarded and a fresh unit or units will be obtained for retention over the following year.

It is therefore, an object of this invention to provide an inexpensive, automatic, disposable hypodermic syringe which can be operated by a layman to inject a medicament.

It is a further object of this invention to provide a syringe of the character described which has a retracted needle prior to administering an injection.

It is yet another object of this invention to provide a syringe of the character described which can be used but once, and is not reusable.

It is an additional object of this invention to provide a syringe of the character described which operates in a dependable manner with a consistent operational sequence.

It is another object of this invention to provide a syringe of the character described wherein the medication is protected against trauma and is maintained for an extended storage period in a sterile condition free from deliterious influences.

It is yet an additional object of this invention to provide a syringe of the character described wherein the internal working components of the syringe are maintained in a sterile condition over an extended period of time.

These and other objects and advantages of the invention will become more readily apparent from the following detailed description of a preferred embodiment thereof taken in conjunction with the accompanying drawings, in which:

FIG. 1 is an elevational view of a preferred embodiment of a hypodermic syringe formed in accordance with the invention;

FIG. 2 is an axial sectional view of the device of FIG. 1 shown in its ready-to-use condition, in which condition it is carried about;

FIG. 3 is a transverse sectional view taken along line 3—3 of FIG. 2;

FIG. 4 is a plan view of one end of a component part of the device of FIG. 1;

FIG. 5 is a fragmented axial sectional view taken along line 5—5 of FIG. 4;

FIG. 6 is an axial sectional view similar to FIG. 2 but showing the device after it has been activated and punctured the user's skin, but before an injection has been delivered;

FIG. 7 is an axial sectional view similar to FIG. 6, but showing the device as it appears when the medication chamber has been initially pierced and the dose is about to be injected;

FIG. 8 is an axial sectional view similar to FIG. 7, but showing the device as it delivers the full injection to the user;

Figure 11:
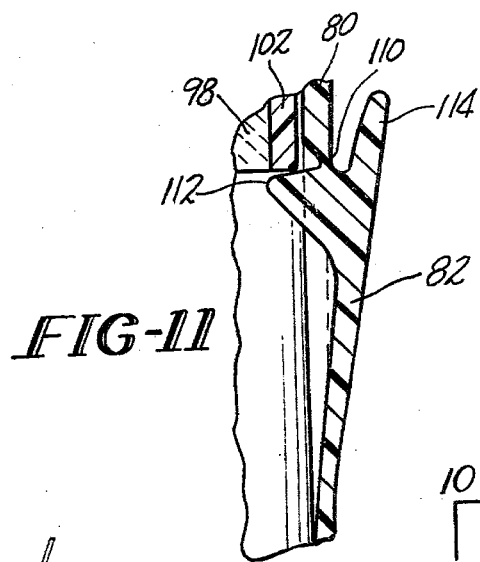
FIG. 11 is an enlarged fragmentary view of a portion to the device shown in FIG. 10.

Referring now to the drawings, there is shown in FIG. 1 a preferred embodiment of a hypodermic syringe made in accordance with the invention. The syringe, denoted generally by the numeral 2, includes a cap 4, the outer surface of which is preferably knurled or otherwise roughened for improved frictional gripping characteristics. The cap 4 is mounted on a guide tube member 6 for unidirectional rotation thereabout. A base 8 is telescoped over the guide tube 6 and is provided with flutes 10 for manually gripping the device. It will be noted that the base 8 could be made integral and in one piece with the guide tube 6, if desired. A strip of sealing tape 12 having a pull tab 14 is adhered to the device 2 so as to cover and seal the joint between the cap 4 and the tube 6. The tape 12 may be made of polyvinyl chloride or the like material which is capable of sealing the joint against moisture, and maintaining the sterile condition of the inner components of the device. A second tape strip 16 of similar material is adhered to the bottom surface of the base 8 to seal off a needle port against passage of moisture therethrough so as to keep the interior of the device sterile. The top of the cap 4 is provided with a retaining loop 18 through which a cord 20 passes. The cord 20 allows the device to be worn conveniently about the neck of the user. The tapes 12 and 16 serve to keep the interior of the device dry and sterile so that it can be worn by the user in any environment, and can even be worn while swimming, or bathing.

Referring now to FIGS. 2–5, the various features of the interior of the device are shown. The lower interior wall of the side of the cap 4 is provided with a resilient tab 22 which interlocks with a tapered lug 24 on the guide tube 6. The interlock extends around substantially the entire periphery of the cap 4 and tube 6. The securement is achieved by merely pressing the cap 4 down onto the tube 6 until the tab 22 slides over and snaps onto the lug 24. The cap 4 may be slotted if necessary to somewhat increase the resiliency of the tab 22. When mounted, the cap 4 can rotate on the tube 6 but cannot easily be pulled longitudinally off the tube. The cap 4 is provided within internal well 26 in which a coil spring 28 is disposed. A spring guide boss 30 can be formed on an appropriate inner surface of the cap 4. A pair of recesses 32 are formed in the inner side wall of the cap 4. A radially outwardly extending shoulder 34 is disposed on the inner side wall of the cap 4 axially adjacent to the recesses 32, the shoulder 34 serving as an abuttment for the upper end wall 36 of the guide tube 6.

The guide tube 6 is formed with an axial through bore 38. Three recesses 40 are formed in the inner wall of the tube 6 adjacent to the upper end wall 36 thereof extending radially outwardly from the bore 38 to form three shoulders 42. The recesses 40 extend through approximately a 60° angle in a clockwise direction and terminate in axially extending slots 44. The slots 44 are disposed angularly with respect to each other in the tube 6, as will be noted in FIG. 4. The ends of the recesses 40 remote from the slots 44 form radial shoulders 45, as will be seen in FIG. 4.

Disposed within the guide tube 6 is a retainer member 46 upon one end of which the coil spring 28 bears. A spring guide boss 31 is formed on the spring-bearing end of the retainer member 46. Three radial lugs 48 are formed on the side wall of the retainer member 46, the lugs 48 being disposed in the guide recesses 40 and in the cap slots 32. As shown in FIG. 2, the retainer lugs 48 are positioned in the guide recesses 40 so as to be in contact with the radial shoulders 45. The lower surface of the retainer 46 is formed with a blind bore 50 which retains an open-ended glass ampoule 52. The ampoule 52 contains an effective dose of a medication at 54, such as adrenalin, and the open end of the ampoule 52 is closed off by a cup-shaped elastomeric piston 56, the piston 56 being operative to seal off the open end of the ampoule 52, but being sized so as to be slidable with the bore of the ampoule 52. The piston 56 is formed with a blind bore 58 the inner end of which is closed off by a web portion 60 which abuts the medication dose 54 so that the medication dose 54 substantially fills the available volume of the ampoule 52.

A hypodermic needle 62 is disposed within the guide tube bore 38, the needle 62 extending through a ferrule 64 which is frictionally press-fitted into the blind bore 58 in the piston 56. The ferrule 64 is formed with a radial flange 66 which is sized so as to be insertable within the ampoule 52. The ferrule flange 66 is normally spaced apart from the end wall of the piston 56. It will be noted that both ends of the needle 62 are provided with beveled points. The lower pointed end of the needle 62 is positioned in an open-ended bore 69 which extends through a pedistal 68 which extends upwardly into the guide tube bore 38 from the base 8 of the device. It will be noted from FIG. 2 that the tape 16 seals off the bore 69. It will further be noted that the upper surface 70 of the pedistal 68 is aligned with the lower surface 72 of the ferrule 64.

Referring now to FIGS. 6-8, the mode of operation of the device is shown. It will be noted that to operate the device, one removes the tape strip 12 from the device by grasping the tape tab 14 and peeling the tape strip 12 off of the device in a counter-clockwise direction. The injection is administered by rotating the cap 4 in a clockwise direction (as viewed from the top of the cap). An indicating arrow (not shown) can be embossed or otherwise placed on the cap top for informational purposes. The actual direction of rotation is unimportant, of course; however, the tape 12 should be pulled in the opposite direction from the direction of cap rotation so as to minimize the possibility of accidental actuation. For purposes of clarity, the bottom portion of the device is shown as being the rotated part, and the cap 4 is shown in the same position in each figure.

Referring briefly to FIG. 2, it will be noted that the device is shown in a cocked condition. In the cocked position, the coil spring 28 is compressed and is held in the compressed condition by the retainer lugs 48 being seated on the shoulders 42. In the cocked position, the retainer 46, ampoule 52 and needle 62 are all in what can be characterized as retracted positions.

To administer the injection, after the tape 12 has been removed, the lower surface 9 of the base 8 is pressed down upon the skin (shown in phantom in FIG. 6) and the cap 4 is twisted or rotated in the clockwise direction. The retainer lugs 48 are thus slid over the shoulder 42 by reason of being held by the cap recesses 32 until a 60° rotation of the cap has been traversed, whereupon the lugs 48 are in registry with the slots 44. The spring 28 then drives the retainer 46 axially through the tube bore 38, the lugs 48 travelling through the slots 44. The retainer 46 and ampoule 52 are thus driven through the tube bore 38 to the position shown in FIG. 6 wherein the lower surface 72 of the ferrule 64 is driven against the upper surface 70 of the pedistal 68, as shown in FIG. 6. Due to the frictional resistance at the ferrule-piston bore joint concurrently, the needle 62 is driven through the closure tape 16 and into the flesh of the user.

The spring 28 continues to drive the retainer 46 downwardly (relatively speaking) so that the ferrule-piston bore joint frictional resistance is overcome and ferrule 64 is forced up into the blind bore 58 of the piston 56 (as shown in FIG. 7). The ferrule 64 carries the needle 62 up into the piston 56 so as to cause the needle 62 to puncture the piston web 60 and enter the medication 54, as shown in FIG. 7. It will be noted that the piston 56 cannot move further into the ampoule 52 until the piston web 60 is punctured due to the substantially incompressible liquid medication 54 resisting such movement of the piston 56.

Once the web 60 is punctured, the needle bore forms an escape path for the medication which is pumped therethrough as the piston 56 is pushed up into the ampoule 52 as a result of the spring 28 pushing the retainer 46 and ampoule 52 toward the surface 9 of the base 8, while the pedistal 68 and ferrule flange 70 combine to hold the piston 56 in place as is shown in FIG. 8. Thus the piston 56 is prevented from moving along with the ampoule 52 as the latter is driven by the spring 28. The action of the ampoule 52 being driven down over the piston 56 after the web 60 has been punctured thus injects the medication into the user. The entire injection process will be achieved in less than one second.

The syringe of this invention will be relatively inexpensive to make as the cap 4, guide tube 6, base 8 and retainer 46 can all be made from suitable injection molded plastic. The spring 28 and needle 62 will be made from metal, and the piston will be made from a relatively elastomeric material, such as butyl rubber, polytetrafluorethylene, or the like. The ampoule 52 will be glass, and the ferrule 64 can be made of metal or rigid plastic. The tapes 12 and 16 will be formed from polyvinyl chloride or the like, as previously noted.

Figure 10:
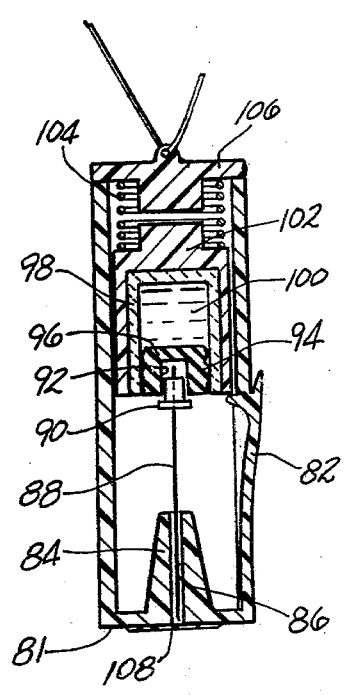
FIG. 10 is an axial sectional view of the device of FIG. 9 taken along line 10—10 thereof.
Figure 9:
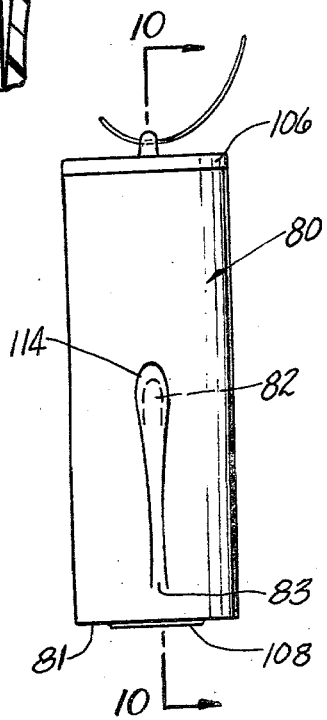
FIG. 9 is a side elevational view of a second embodiment of a syringe formed in accordance with this invention.

Referring now to FIGS. 9-11, a second embodiment of the syringe of this invention is disclosed. The device includes a guide tube 80 which is injection molded with an integral actuating trigger 82 formed in its side wall. The inside of the lower end of the guide tube 80 has a pedistal 84 with a through bore 86 in which the hypodermic needle 88 is positioned. The needle 88 is fitted with a ferrule 90 as previously described. The ferrule 90 is fitted into a blind bore 92 of an elastomeric piston 94 the piston bore 92 being closed with a web 96. The piston 94 is positioned in an ampoule 98 to seal the open end thereof, thereby forming a chamber which contains a dose of medication 100. The ampoule 98 is set in a retainer 102 against which one end of a spring 104 bears, the other end of the spring 104 is seated against a cap member 106. The cap member 106 is secured tightly to the guide tube 80, by means of an adhesive, sonic welding, or the like. A tape 108 seals the lower end of the bore 86.

It will be noted that the trigger 82 is molded in one piece with the rest of the guide tube 80 and is connected thereto by a thin walled web 110 which extends around most of the periphery of the trigger 82, except for the lowermost end 83 thereof. The upper inside part of the trigger 82 is formed with a catch 112 which projects into the tube 80 and against which the retainer 102 is biased. The upper outside part of the trigger 82 is formed with a finger-engaging portion 114 which is spaced outwardly from the outer wall of the guide tube 80, as is shown in FIG. 11. The syringe is shown, as is apparent, in the cocked condition, sealed and ready for use. To use the syringe, the lower surface 81 of the guide tube 80 is pressed lightly against the patients flesh and the finger-engaging portion 114 is pressed inwardly toward the guide tube 80. This breaks the thin-walled web 110 while retaining the catch 112 beneath the retainer 102. The trigger 82 is then pulled outwardly by grasping the portion 114. The catch 112 is thus pulled out from beneath the retainer 102. The spring 104 then drives the retainer 102, ampoule 98 and needle 88 downwardly, and the injection is administered as previously described.

Sterile assembly of the syringe 2 of FIGS. 1-8 is accomplished as follows. The glass ampoule 52 is filled with the appropriate drug dosage and closed with the piston 56 in a sterile atmosphere. Thereafter, the ampoule-piston sub-assembly may be handled in a non-sterile environment without affecting the sterility of the drug.

The ampoule 52 is then affixed to the retainer 46 with a friction fit, or by means of an adhesive. The needle-ferrule assembly 62, 64 is then fitted to the piston-ampoule assembly 56, 54.

The needle ferrule 64, ampoule 52, retainer 46, piston 56 assembly is then placed in the guide tube 6, base 8 pre-assembly in the positions shown in FIG. 1. The spring 28 and cap 4 are then added, along with the tape 12. The partially assembled unit is then sterilized in a sterilization unit, or the like and the final tape 16 is then added to seal the entire unit, and to maintain the internal portion thereof in a sterile condition.

With respect to the second embodiment of the device shown in FIGS. 9–11, the preferred mode of sterile assembly is as follows. The ampoule 98, retainer 102, piston 94, needle 88 sub-assembly is constructed as outlined above. This sub-assembly is then positioned inside of the tube 80, and the spring 104 dropped on atop thereof. The cap 106 is then pressed on top of the spring and secured to the tube 80 by means of a suitable adhesive, sonic welding, or the like. The partially assembled device is then placed as an autoclave, gas sterilization unit, or the like, where the tape 108 is added, whereby the unit is maintained in a sterile condition.

It will be appreciated that in some applications, the ampoule could be an annular sleeve with one end closed by the piston and the other end closed by a compatible seal member.

It will be readily appreciated that the device of this invention is inexpensive to manufacture, useful for administering emergency or non-emergency injections, and compact and sturdy enough to be carried about on one's person. The device remains moisture-tight and sterile without any special packaging. The device can be used by a layman to self-inject the medication, thereby enhancing its usefulness in emergency situations.

While the syringe of this invention is particularly useful in self-administering injections, it also has wide application in other situations. For example, it can be used by trained personnel in hospitals, physicians' offices, etc. to give injections of all types of drugs minimizing dosage errors. It is felt that the device will reduce the trauma of receiving an injection, especially in children, since the needle is not seen.

The separably sterilizable feature of this device is achieved by use of an ampoule which is filled with the medication and closed with a compatible elastomeric piston or pistons, the ampoule-medicament-piston sub-assembly being assembled in a sterile environment in a mass assembly fashion. The remainder of the components do not have to be sterilized until after the device is completely assembled except for the tape or tapes. Thus, the device is susceptible of being mass-assembled. The ability of the device to store a medication safely for an extended period of time is achieved by using the glass-elastomeric piston sterile sub-assembly and by keeping the needle out of the medication until the injection is actually administered. The durability of the device is achieved by forming the external parts of the device from tough plastic material and by housing and protecting the glass medicament ampoule inside of the external plastic parts. In some instances, it may be desirable to form the ampoule-carrier assembly from a single molded piece of glass, or, where medicament compatability permits, from an inert plastic, such as polytetrafluoroethylene, UHMW polyethylene, or the like. The repeatable injection sequence achieved by the device is obtained by using the ferrule-piston sub-assembly in combination with the elastomeric piston-ampoule sub-assembly so that the ampoule-piston drives the needle into the user's flesh to the full injection depth before the needle punctures the piston to enter the medication. This feature also greatly simplifies the construction of the device.

The inability to use the device more than once is the result of several features. Once assembled, the device cannot be opened to reset the mechanism without destroying its ability to operate. Furthermore, the piston cannot be withdrawn from the ampoule once the device has been used without destroying the integrity of the piston. Finally, the ferrule prevents the needle from being withdrawn from the device after an injection is administered.

Perhaps the most important aspect of the design of the second embodiment is its low manufacturing cost. To be commercially acceptable as a dispenser for unit-dose injected medicaments, the cost of manufacture must not be too much in excess of that of a standard disposable syringe plus the required medicament. In the prior art, the complex nature of the syringe housings and release mechanisms necessitates a higher manufacturing cost. The features of the second embodiment enable it to be produced at a relatively low cost.

In large production quantities, it is important that both the number of parts to be assembled be kept to a minimum and that the mold required to make them be kept as simple as possible. For example, a complex mold which requires a one-minute disassembly and set-up time is far more costly to run than one which takes only fifteen seconds. The simple release catch in the second embodiment allows for lower manufacturing costs as compared to the prior art.

As stated earlier, one of the features of the second embodiment is that it is a self-contained sealed unit which requires no further containment to maintain its internal sterility. This feature allows it to be readily carried about with the user without concern for contamination. In some instances, however, this feature is not necessary, such as when the unit is stocked and used in a hospital or at home for use by a diabetic. In these and like instances, the design of the second embodiment can be slightly altered in the following manner to further reduce mold complexity, and therefore, manufacturing cost.

The release catch 82 could be molded as an integral part of a separately molded basal end cap (81, 84). The catch and end cap part would then be attached to the body 80 in a separate operation. Although this would require another assembly step, it would eliminate molding "undercuts", thus greatly simplifying mold design. Although the imperforate web 110 would not be present in this production method, the finished unit could be sealed in a sterile package, such as a foil or plastic-paper laminate. With this packaging method, tape seal 108 would, of course, be eliminated.

Since many changes and variations of the disclosed embodiments of the invention may be made without departing from the inventive concept it is not intended to limit the invention otherwise than as required by the appended claims.

What is claimed is:

1. An automatic disposable hypodermic syringe capable of storing a medicament for an extended period of time, said syringe comprising:

(a) a compact housing comprising a tubular part, a cap closing one end of said tubular part, and a base closing the other end of said tubular part;

(b) means securing said tubular part to said cap and said base to prevent ready disassembly of said housing;

(c) an ampoule disposed in said tubular part for movement between a first position and a second position, said ampoule having a closed basal end and an opposite open end, said ampoule containing a dose of a medicament;

(d) an imperforate elastomeric piston disposed in and sealing said open end of said ampoule;

(e) spring means within said housing for biasing said ampoule from said first position to said second position;

(f) catch means within said housing for retaining said ampoule in said first position against the bias of said spring means, said catch means being formed as an integral part of said tubular member and being partially surrounded by a thin-walled web of material which can be ruptured by applying pressure to said catch means;

(g) actuating means formed as a manually graspable portion of said tubular member integral with said catch means, said actuating means being manually operable from the exterior of said housing for neutralizing said catch means whereby said ampoule can be released and driven by said spring means to said second position;

(h) a hypodermic needle within said housing, said needle being movable between a retracted position wherein said needle is completely contained within the confines of said housing, and an injecting position wherein said needle protrudes through an opening in said base;

(i) a ferrule secured to said needle and telescopingly connected to said piston, said ferrule being movable with respect to said piston between a first frictionally retained position wherein said needle is held out of contact with said piston and completely isolated from said medicament, and a second abutting position wherein said needle extends through said piston and into said medicament; said ferrule being in said first position when said needle is in said retracted position;

(j) means on said base for engaging said ferrule after said needle has been driven to said injecting position, said means being operable to hold said needle in said injecting position and cause said ferrule to move to said second abutting position; and (k) sealing means for closing all joints and openings in said housing to retain a sterile condition within said housing.

2. An automatic disposable hypodermic syringe capable of storing a medicament for an extended period of time, said syringe comprising:

(a) a compact tubular housing, both ends of which are sealed, one of said ends being a basal end;

(b) an ampoule disposed in said housing, said ampoule containing a medicament and having an open end facing said basal end of said housing, said open end being sealed by an imperforate elastomeric piston;

(c) a hypodermic needle contained completely within the confines of said housing, said needle being connected to said piston and said needle being isolated from contact with said medicament by said piston;

(d) said needle and said ampoule being in a cocked retracted position within said housing, but being movable to an injecting position wherein said needle protrudes from said housing through said needle port;

(e) spring means in said housing for biasing said ampoule and said needle toward said injecting position; and (f) a catch projecting into said housing for holding said ampoule and said needle in said cocked position against the bias of said spring means, said catch being formed as an integral part of said housing, and said catch being partially surrounded by an impermeable thin walled portion of said housing, said portion of said housing being rupturable when a deflecting force is manually applied to said catch.

3. An automatic disposable hypodermic syringe capable of storing a medicament for an extended period of time, said syringe comprising:

(a) a compact substantially tubular housing, said housing including end closure means substantially irremovably connected to said housing to prevent dissassembly of said housing;

(b) one of said end closure means including a thin-walled impermeable membrane susceptable to being pierced by a needle;

(c) a needle in said housing, said needle having sharpened points at both ends thereof;

(d) a ferrule fixed to said needle;

(e) an ampoule disposed in said housing for movement between a first position and a second position therein, said ampoule containing an effective amount of a medicament, said ampoule having one fixed end closure and one movable end closure, at least one of said end closures being an impermeable elastomeric membrane;

(f) means for engaging said ferrule to prevent said needle from puncturing said elastomeric membrane until said needle has been driven through said thin-walled impermeable membrane to an injecting position;

(g) spring means within said housing for biasing said ampoule from said first position to a second position;

(h) catch means within said housing for retaining said ampoule in said first position against the bias of said spring means, said catch means being formed as an integral part of said housing and being partially surrounded by an impermeable thin-walled portion of said housing which thin-walled portion is rupturable when a deflecting force is applied to said catch means manually;

(i) actuating means integral with said catch means and manually operable from the exterior of said housing for neutralizing said catch means whereby said ampoule can be released and driven by said spring means to said second position; and (j) sealing means for closing all joints and openings in said housing to retain a sterile condition within said housing.

4. An automatic disposable hypodermic syringe capable of storing a medicament for an extended period of time, said syringe comprising:

(a) a compact tubular housing, both ends of which are provided with transverse end walls, one of said end walls providing a basal end having a restricted needle port extending therethrough;

(b) an ampoule disposed in said housing, said ampoule containing a medicament and having an open end facing said basal end of said housing, said open end being sealed by an imperforate elastomeric piston;

(c) a hypodermic needle contained completely within the confines of said housing, said needle being connected to said piston and said needle being isolated from contact with said medicament by said piston;

(d) said needle and said ampoule being in a cocked retracted position within said housing, but being movable to an injecting position wherein said needle protrudes from said housing through said needle port;

(e) spring means in said housing for biasing said ampoule and said needle toward said injecting position; and (f) a catch projecting into said housing for holding said ampoule and said needle in said cocked position against the bias of said spring means, said catch being radially outwardly movable to release said ampoule and needle for movement to said injecting position, and said catch being formed as an integral part of said housing and being partially surrounded by an impermeable thin-walled rupturable portion of said housing.

* * * * *